United States Patent [19]

Häusermann et al.

[11] Patent Number: 4,977,169
[45] Date of Patent: Dec. 11, 1990

[54] N-3-(5-TRIFLUOROMETHYLPYRIDYL-2-OXY)PHENYL-N'-BENZOYLUREAS FOR CONTROLLING HELMINTHS IN PRODUCTIVE LIVESTOCK

[75] Inventors: Walter Häusermann, Ollon; Max Maurer, Murten, both of Switzerland; Thomas Friedel, N.S.W., Australia

[73] Assignee: Ciba-Geigy Corporation, Ardsley, N.Y.

[21] Appl. No.: 352,085

[22] Filed: May 15, 1989

Related U.S. Application Data

[63] Continuation-in-part of Ser. No. 5,511, Jan. 20, 1987, abandoned.

[30] Foreign Application Priority Data

| Jan. 21, 1986 | [CH] | Switzerland | 222/86 |
| Apr. 8, 1986 | [CH] | Switzerland | 1362/86 |
| Dec. 17, 1986 | [CH] | Switzerland | 5053/86 |

[51] Int. Cl.⁵ .............................. A01N 43/40
[52] U.S. Cl. .......................... 514/346; 546/291
[58] Field of Search ............ 546/300, 291; 514/351, 514/346

[56] References Cited

U.S. PATENT DOCUMENTS

| 4,418,066 | 11/1983 | Böger et al. | |
| 4,677,127 | 6/1987 | Boger | 514/346 |

FOREIGN PATENT DOCUMENTS

| 0079311 | 5/1983 | European Pat. Off. |
| 8603941 | 7/1986 | PCT Int'l Appl. |
| 1464553 | 2/1977 | United Kingdom |
| 2110672 | 3/1986 | United Kingdom |

OTHER PUBLICATIONS

Chem. Abstract, 99:38380f (1983).
Chem. Abstract, 99:88061y (1983).

*Primary Examiner*—Mukund J. Shah
*Assistant Examiner*—Philip Datlow
*Attorney, Agent, or Firm*—Kevin T. Mansfield; George R. Dohmann

[57] ABSTRACT

The invention relates to the use of N-3-(5-trifluoromethylpyridyl-2-oxy)phenyl-N'-benzoylureas of formula I

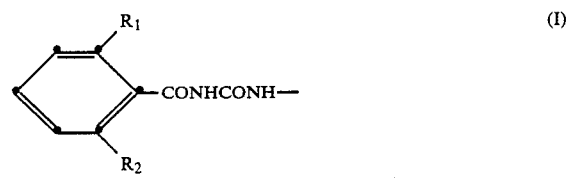

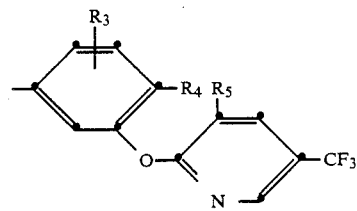

wherein
$R_1$ is hydrogen, $C_1$–$C_2$alkoxy, $C_1$–$C_2$alkylthio, $C_1$–$C_2$alkyl or halogen,
$R_2$, $R_3$ and $R_5$ are independently of each other hydrogen or halogen, and
$R_4$ is hydrogen, $C_1$–$C_2$alkyl or halogen,
for controlling helminths, especially nematodes and trematodes, in domestic animals and productive livestock.

10 Claims, No Drawings

N-3-(5-TRIFLUOROMETHYLPYRIDYL-2-OXY)-PHENYL-N'-BENZOYLUREAS FOR CONTROLLING HELMINTHS IN PRODUCTIVE LIVESTOCK

This is a CIP of Ser. No. 5,511, filed Jan. 20, 1987, now abandoned.

The present invention relates to N-3-(5-trifluoromethylpyridyl-2-oxy)phenyl-N'-benzoylureas as defined in formula I below for controlling helminths, especially nematodes and trematodes, in domestic animals and productive livestock, preferably in warm-blooded animals and, first and foremost, in mammals.

The N-3-(5-trifluoromethylpyridyl-2-oxy)phenyl-N'benzoylureas of this invention have the formula I

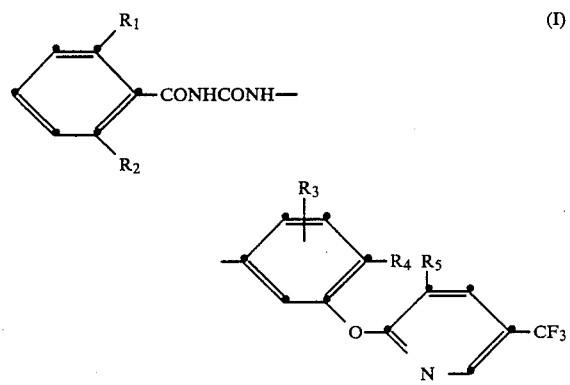

wherein
$R_1$ is hydrogen, $C_1$-$C_2$alkoxy, $C_1$-$C_2$alkylthio, $C_1$-$C_2$alkyl or halogen,
$R_2$, $R_3$ and $R_5$ are independently of each other hydrogen or halogen, and
$R_4$ is hydrogen, $C_1$-$C_2$alkyl or halogen.

Preferred compounds of formula I are those wherein
$R_1$ is fluorine, chlorine, methoxy, methylthio or methyl,
$R_2$ is hydrogen, fluorine or chlorine,
$R_3$ is hydrogen, 2-fluoro or 2-chloro,
$R_4$ is hydrogen, fluorine, chlorine, bromine or methyl, and
$R_5$ is fluorine or chlorine.

Particularly preferred compounds of formula I are those wherein
$R_1$ is fluorine, methoxy or methylthio,
$R_2$ is fluorine,
$R_3$ is hydrogen,
$R_4$ is fluorine, chlorine or bromine, and
$R_5$ is chlorine.

$C_1$-$C_2$Alkyl by itself or as moiety of alkoxy or alkylthio is methyl or ethyl, so that $C_1$-$C_2$alkoxy is ethoxy or methoxy and $C_1$-$C_2$alkylthio is ethylthio or methylthio. Halogen is fluorine, chlorine, bromine or iodine, with fluorine, chlorine or bromine being preferred.

Preferred individual compounds of formula I are e.g.:

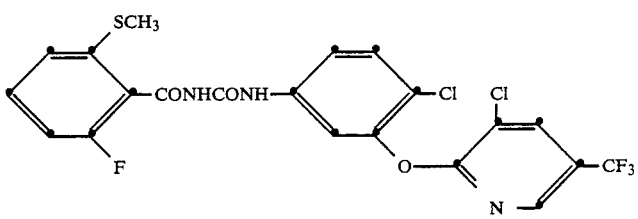

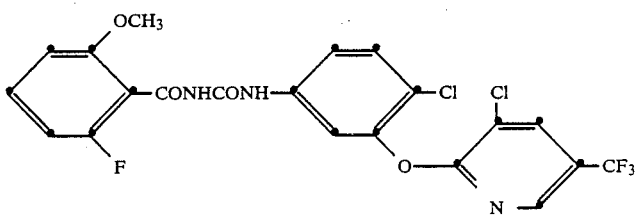

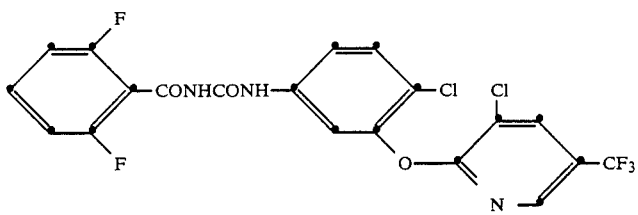

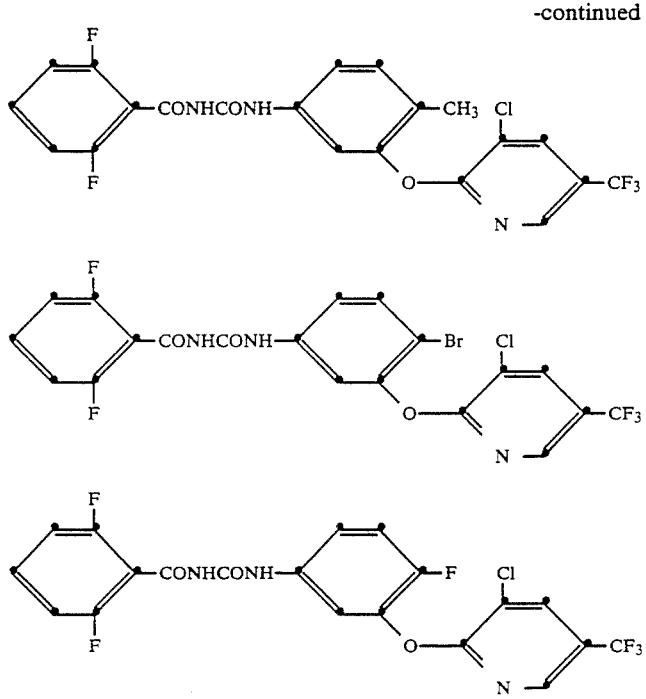

Further typical representatives of compounds of formula I are:

| Compound No. | R₁ | R₂ | R₃ | R₄ | R₅ |
|---|---|---|---|---|---|
| 1 | F | F | H | CH₃ | Cl |
| 2 | F | F | H | H | H |
| 3 | Cl | H | H | H | H |
| 4 | F | F | H | Br | Cl |
| 5 | Cl | Cl | H | Br | Cl |
| 6 | Cl | H | H | Br | Cl |
| 7 | Cl | H | H | CH₃ | Cl |
| 8 | H | H | H | CH₃ | Cl |
| 9 | F | F | H | Br | H |
| 10 | CH₃ | H | H | CH₃ | H |
| 11 | Br | H | H | CH₃ | Cl |
| 12 | CH₃ | H | H | CH₃ | Cl |
| 13 | Cl | H | H | CH₃ | H |
| 14 | Br | Br | H | CH₃ | Cl |
| 15 | F | F | H | CH₃ | H |
| 16 | F | F | H | F | Cl |
| 17 | F | F | H | Cl | Cl |
| 18 | F | F | H | F | H |
| 19 | F | F | H | Cl | H |
| 20 | H | H | 2-Cl | H | Cl |
| 21 | H | F | 2-Cl | Cl | Cl |
| 22 | F | Cl | 2-Cl | H | Cl |
| 23 | F | F | H | C₂H₅ | Cl |
| 24 | OCH₃ | F | H | Cl | Cl |
| 25 | OCH₃ | F | H | CH₃ | Cl |
| 26 | OCH₃ | F | H | C₂H₅ | Cl |
| 27 | OC₂H₅ | F | H | Cl | Cl |
| 28 | SCH₃ | F | H | Cl | F |
| 29 | SCH₃ | F | H | CH₃ | Cl |
| 30 | SCH₃ | F | H | C₂H₅ | Cl |
| 31 | SCH₃ | F | H | Cl | Cl |
| 32 | SC₂H₅ | F | H | Cl | Cl |
| 33 | Cl | Cl | H | Cl | Cl |
| 34 | F | F | H | Cl | Br |
| 35 | F | F | 2-Cl | Cl | Cl |
| 36 | F | F | 3-Cl | Cl | Cl |
| 37 | F | F | 2-F | Cl | Cl |
| 38 | F | F | 2-Br | F | Cl |
| 39 | F | Br | H | Cl | Cl |
| 40 | Cl | H | H | Cl | H |
| 41 | Cl | H | H | Cl | Cl |

In PCT patent application WO-86/03941, the entire chemical field of acylureas is broadly claimed for controlling all conceivable endo- and ectoparasites in warm-blooded animals. Almost all known dimiloids are either listed or incorporated by reference. The listed compounds include compound No. 17 of the present application [see page 106, the seventh compound]. However, biological data with respect to specific activities are cited for only a few individual compounds of a specific structural pattern and these data diverge very broadly. With respect to the anthelmintic activity of dimiloids characterized by a 3-chloro-5-trifluoromethyl-2-pyridyloxy group there are data given only for one single representative namely for 1-[4-(3-chloro-5-trifluoromethyl-2-pyridyloxy)-2,5-dichlorophenyl]-3-(2,6-difluorobenzoyl)urea that is compound No. 11 (page 145 of the PCT application) that exhibits according to example 22 on pages 200ff a percent mortality of only 33. Therefore, there is no teaching of anthelmintic activity in the specific subclass of dimiloids claimed in the present application.

The compounds of formula I are known from European patent application EP-79311 as parasiticides for controlling ectoparasites of the class of insects as well as of the order Acarina, or they can be prepared as disclosed therein. However, neither EP 79311 nor EP 79311 in combination with WO 86/03941 suggests that the present compounds would be as effective as disclosed in the present application namely in controlling parasites such as helminths belonging to totally different taxonomic units than the arthropods insects and Acarina of EP 79311. Since the classification follows the degree of similarity the affiliation to far distant units reflects the disparity in morphological as well as in physiological and biochemical traits. A compound being active in controlling arthropods does by no means lead to the assumption that this same compound may be equally qualified for the control of helminths. Thus, it was very surprising to find a subclass within the dimiloids exhibiting this extraordinary high anthelmintic activity.

The compounds of formula I can be obtained by reacting for example (a) a compound of formula II

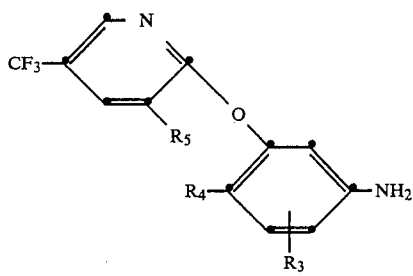

with a compound of formula III

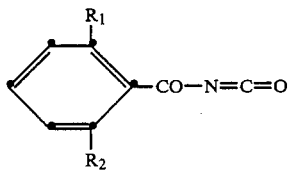

or by reacting (b) a compound of formula IV

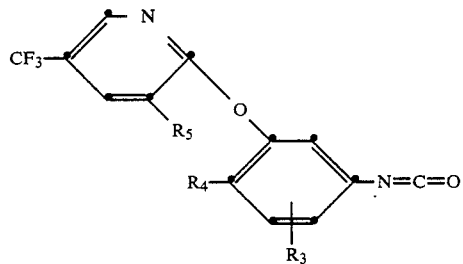

with a compound of formula V

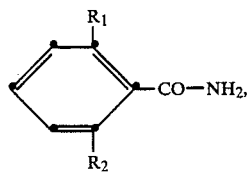

in the absence or presence of an organic or inorganic base, or by reacting (c) a compound of formula II with a compound of formula VI

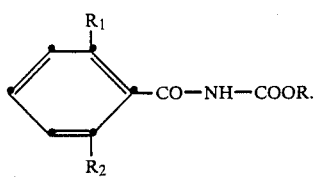

In the formulae II to VI above, the substituents $R_1$ to $R_5$ are as defined for formula I and R is a $C_1$–$C_8$alkyl radical or a halogen-substituted $C_1$–$C_8$alkyl radical.

The above processes (a), (b) and (c) may conveniently be carried out under normal pressure and in the presence of an organic solvent or diluent. Examples of suitable solvents or diluents are: ethers and etheral compounds such as diethyl ether, dipropyl ether, dibutyl ether, dioxane, dimethoxyethane and tetrahydrofuran; N,N-dialkylated carboxamides; aliphatic, aromatic and halogenated hydrocarbons, especially benzene, toluene, xylene, chloroform, methylene chloride, carbon tetrachloride and chlorobenzene; nitriles such as acetonitrile or propionitrile; dimethyl sulfoxide; and ketones, e.g. acetone, methyl ethyl ketone, methyl isopropyl ketone and methyl isobutyl ketone. Process (a) is normally carried out in the temperature range from $-10°$ to $+100°$ C., preferably from 15° to 25° C., and if desired in the presence of an organic base, e.g. triethylamine. Process (b) is carried out in the temperature range from 0° to 150° C., preferably at the boiling point of the solvent employed and, if desired, in the presence of an organic base such as pyridine, and/or with the addition of an alkali metal or alkaline earth metal, preferably sodium. For the reaction of the urethane of formula VI with the aniline of formula II according to process (c), a temperature range from about 60° to the boiling point of the reaction mixture is preferred, and the solvent employed is preferably an aromatic hydrocarbon such as toluene, xylene, chlorobenzene or the like.

The starting materials of formulae II to VI are known and can be prepared by methods analogous to known ones. Some of the starting compounds of formula II and IV are novel compounds which can be prepared by methods that are known per se (q.v. for example U.S. Pat. Nos. 3,705,170 and 3,711,486).

5-Trifluoromethylpyridyl-2-oxyanilines of formula II can be prepared as follows:

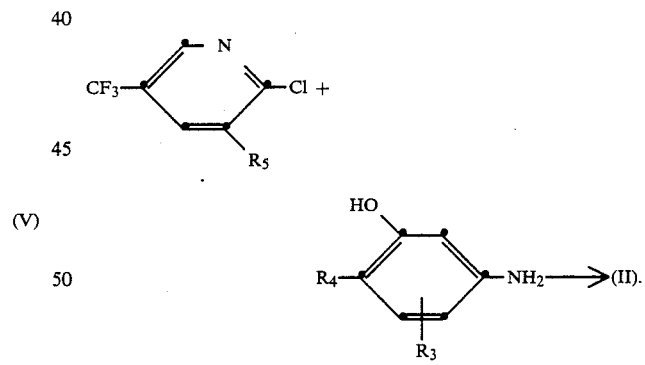

This reaction is carried out in the temperature range from 20°–180° C., preferably from 50°–160° C., in the presence of an acid acceptor, e.g. a hydroxide or hydride of an alkali metal or alkaline earth metal, preferably KOH or NaOH, as well as of an inert organic solvent, preferably dimethylformamide or dimethylsulfoxide. Further, an aniline of formula II can be obtained by a process analogous to that described in J. Org. Chem. 29 (1964), 1, by hydrogenating the corresponding nitro compounds (cf. the literature cited therein). Anilines of formula II are also obtainable by chemical reduction (e.g. with Sn(II) chloride/HCl) of a corresponding nitro compound (cf. Houben-Weyl, Methoden d. org. Chemie, 11-/1, 422, 1957):

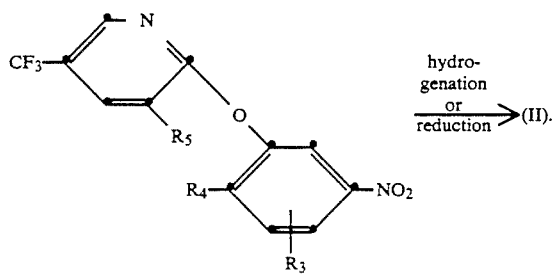

Benzoylisocyanates of formula III can be obtained, inter alia, as follows (q.v. J. Agr. Food Chem. 21, 348 and 993; 1973):

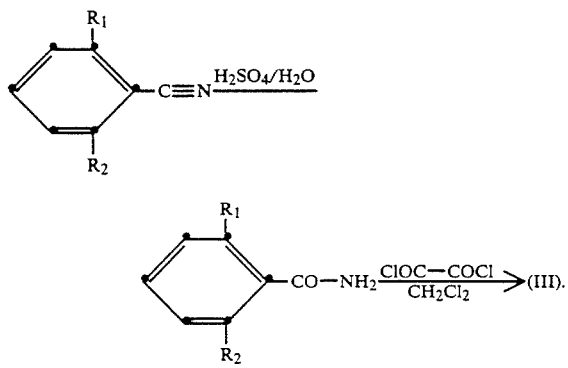

A 3-(5-trifluoromethylpyridyl-2-oxy)phenylisocyanate of formula IV can be prepared e.g. by phosgenating an aniline of formula II by conventional methods. The starting benzamides of formula V are known (q.v. for example Beilstein, Handbuch der organischen Chemie, Vol. 9, p. 336, 1970).

Urethanes of formula VI can be obtained in a manner known per se by reacting a benzoylisocyanate of formula III with an appropriate alcohol or by reacting a benzamide of formula V in the presence of a basic compound with a corresponding ester of chloroformic acid.

Surprisingly, the compounds of formula I have a very useful activity spectrum against parasiticising helminths in the animal organism, especially in warm-blooded animals, most particularly in mammals. They can be used very successfully against nematodes and trematodes. A distinguishing feature of these compounds is in particular that they are fully effective against species which are resistant to benzimidazoles, especially to thiabendazole. By "thiabendazole" is meant e.g. the compound 2-[4-thiazolyl]benzimidazole as well as related compounds of this class. The anthelmintic activity of the compounds of formula I rests less on controlling adult, parasitic forms in the body of the host animal than on inhibiting the development of larvae and on the eggs excreted with the faeces, so that the life cycle of the parasite is effectively interrupted.

Among the endoparasites which occur in warm-blooded animals, the helminths cause severe damage. For example, animals attacked by these parasites are not only retarded in their growth, but in some cases suffer such harmful physiological effects that they die. It is therefore of great importance to develop therapeutic agents which are suitable for controlling helminths and their development stages and to prevent attack by these parasites. Particularly dangerous helminth infestations are those caused in the gastrointestinal tract and other organs by parasitic nematodes, cestodes and trematodes, and especially in ruminants such as sheep, cattle and goats, as well as horses, pigs, deer, dogs, cats and poultry.

The damage caused by helminthiases can be substantial whenever herds of cattle fall victim to chronic and, in particular, to epidemic attack. Such damage takes the form, inter alia, of diminution of useful performance, weakened resistance and increased mortality. The control and prevention of helminth infestation are therefore of the utmost importance to avoid or reduce such damage, especially damage having serious economic consequences.

Throughout this specification, the term "helminths" will be understood as meaning in particular parasitic worms which belong to the Phyla Platyhelminthes (cestodes, trematodes) and Nemathelminthes (nematodes and related species), i.e. cestodes, trematodes and nematodes of the gastrointestinal tract and other organs (e.g. liver, lungs, kidneys, lymphatic vessels, blood etc.). Although a range of compounds having anthelminthic activity are known and have been proposed for controlling the different helminth species, they are not entirely satisfactory, either because it is not possible to exploit their activity spectrum fully when administered in well tolerated doses or because they exhibit undesirable side-effects or characteristics when administered in therapeutic doses. In this regard, the increasing resistance being encountered at the present time to specific classes of compound is an ever more significant factor. Although, for example, the commercial compound "albendazole" (British patent specification 1 464 326; Am. J. Vet. Res. 38, 1425–1426 (1977); Am. J. Vet. Res. 37, 1515–1516 (1976); Am. J. Vet. Res. 38, 807–808 (1977); Am. J. Vet. Res. 38, 1247–1248 (1977)) has a limited activity spectrum as anthelmintic when administered to ruminants, its activity e.g. against benzimidazole-resistant nematodes and adult liver flukes is inadequate. In particular, the pathologically important immature migratory forms of the last mentioned parasites are not attacked when the compound is administered in doses which are tolerated by the host animal.

Surprisingly, it has now been found that the compounds of formula I have not only—as already mentioned—a potent anthelmintic activity with a broad activity spectrum against nematodes, cestodes and trematodes, but, in addition, a low toxicity to warm-blooded animals.

The eligible compounds of formula I are suitable e.g. for controlling parasitic nematodes of the orders (according to the classification of K.I. Skrajabin) Rhabditida, Ascaridida, Spirurida and Trichocephalida or for controlling cestodes of the orders (according to the classification of Wardle and McLeod) Cyclophyllidae and Pseudophyllidae or for controlling trematodes of the order Digenea in domestic animals and product livestock such as cattle, sheep, goats, horses, pigs, cats, dogs and poultry. The compounds of formula I can be administered to the animals in both individual and repeated doses. Depending on the species of animal, the individual doses are preferably administered in amounts ranging from 1 to 500 mg per kg of body weight. A better activity is sometimes achieved by protracted administration, or lower doses may suffice.

The compounds of the formula I are preferably used together with the adjuvants conventionally employed in the art of formulation, and can therefore be formulated in known manner to emulsifiable concentrates, directly sprayable or dilutable solutions, dilute emulsions, wettable powders, soluble powders, dusts, granulates, and also encapsulations in e.g. polymer substances, and to tablets, pellets or boluses.

The formulations, i.e. the compositions containing one or more anthelmintic compounds of formula I and, where appropriate, solid or liquid adjuvants, are prepared in known manner, e.g. by homogenously mixing and/or grinding the active ingredient with extenders, e.g. solvents, solid carriers and, in some cases, surface-active compounds (surfactants).

The following formulation adjuvants are employed for preparing the anthelmintic compositions of the invention: solid carriers, e.g. kaolin, talc, bentonite, common salt, calcium phosphate, carbohydrates, cellulose powder, cottonseed meal, polyethylene glycol ether, optionally binders such as gelatin, soluble cellulose derivatives, if desired with the addition of surface-active compounds such as ionic or non-ionic dispersants; natural mineral fillers such as calcite, montmorillonite or attapulgite. To improve the physical properties it is also possible to add highly dispersed silicic acid or highly dispersed adsorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant material.

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

Suitable surface-active compounds are nonionic, cationic and/or anionic surfactants having good emulsifying, dispersing and wetting properties. The term "surfactants" will also be understood as comprising mixtures of surfactants.

Suitable anionic surfactants can be water-soluble soaps as well as water-soluble synthetic surfactants.

Suitable soaps are the alkali metal salts, alkaline earth metal salts or unsubstituted or substituted ammonium salts of higher fatty acids ($C_{10}$-$C_{22}$), e.g. the sodium or potassium salts of oleic or stearic acid, or of natural fatty acid mixtures which can be obtained e.g. from coconut oil or tall oil.

Frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$-$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine-propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$-$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual" MC Publishing Corp., Ridgewood, N.J., 1981; and Helmut Stache, "Tensid-Taschenbuch" (Handbook of Surfactants), Carl Hanser Verlag, Munich/Vienna, 1981.

Suitable binders for tablets and boluses are chemically modified natural polymers which are soluble in water or alcohol, e.g. starch, cellulose or protein derivatives (e.g. methyl cellulose, carboxymethyl cellulose, ethyl hydroxyethyl cellulose, proteins such as zein, gelatin and the like), as well as synthetic polymers such as polyvinyl alcohol, polyvinyl pyrrolidone etc. Tablets also contain fillers (e.g. starch, microcrystalline cellulose, sugar, lactose etc.), glidants and disintegrators.

If the anthelmintic compositions are in the form of feed concentrates, then suitable carriers are for example production feeds, cereal feeds or protein concentrates. In addition to the active ingredient, such feeds can contain additives, vitamins, antibiotics, chemotherapeutical agents or other pesticides, in particular bacteriostats, fungistats, coccidiostats or also hormone preparations, substances having anabolic action or other substances which promote growth, enhance the quality of the flesh of slaughter animals, or which are otherwise beneficial to the organism. If the compositions or the compound of formula I contained therein are added direct to the solid or liquid feed, then the ready prepared feed contains the active ingredient preferably in a concentration of about 0.0005 to 0.02 percent by weight (5–200 ppm).

The compositions of the invention are administered to the animals to be treated perorally, parenterally, subcutaneously or topically, and are in the form of solutions, emulsions, suspensions (drenches), powders, tablets, boluses and capsules.

The anthelmintic compositions usually contain 0.1 to 99% by weight, preferably 0.1 to 95% by weight, of a compound of formula I, 99.9 to 1% by weight, preferably 99.9 to 5% by weight, of a solid or liquid adjuvant, and 0 to 25% by weight, preferably 0.1 to 25% by weight, of a surfactant.

Whereas commercial products will be preferably formulated as concentrates, the end user will normally employ dilute formulations.

The compositions may also contain further ingredients such as stabilisers, antifoams, viscosity regulators, binders, tackifiers as well as fertilisers or other active ingredients for obtaining special effects.

Such anthelmintic compositions employed by the end user likewise constitute an object of the present invention.

The invention is illustrated in more detail by the following non-limitative Examples.

PREPARATORY EXAMPLES

Example 1: Preparation of
N-3-(3-chloro-5-trifluoromethylpyridyl-2-oxy)-4-chlorophenyl-N'-2,6-difluorobenzoylurea

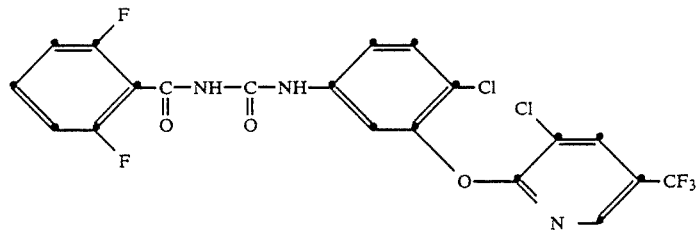

(I)

With stirring, a solution of 3.7 g of 2,6-difluorobenzoylisocyanate in 25 ml of anhydrous toluene is added dropwise to 6.5 g of 3-(3-chloro-5-trifluoromethylpyridyl-2-oxy)-4-chloroaniline in 50 ml of anhydrous toluene. After the initially exothermic reaction has subsided, the reaction mixture is allowed to stand for ca. 24 hours at room temperature, whereupon colourless crystals precipitate. These crystals are isolated by filtration, washed with hexane and recrystallised from toluene/hexane, affording 4.1 g of N-3-(3-chloro-5-trifluoromethylpyridyl-2-oxy)-4-chlorophenyl-N'-2,6-difluorobenzoylurea with a melting point of 217°–218° C. (compound 17).

Example 1.1: Preparation of
N-3-(3-chloro-5-trifluoromethylpyridyl-2-oxy)-4-methylphenyl-N'-2,6-difluorobenzoylurea

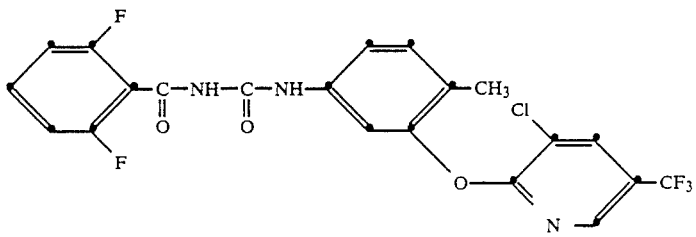

A solution of 2.7 g of 2,6-difluorobenzoylisocyanate in 20 ml of anhydrous toluene is added to 4.5 g of 3-(3-chloro-5-trifluoromethylpyridyl-2-oxy)-4-methylaniline in 50 ml of anhydrous toluene. After the initially exothermic reaction has subsided, the mixture is left to stand overnight. The precipitate is isolated by filtration and washed with hexane, affording white crystals of N-3-(3-chloro-5-trifluoromethylpyridyl-2-oxy)-4-methylphenyl-N'-2,6-difluorobenzylurea with a melting point of 178°–179° C. (compound 1).

Preparation of the starting material

A solution of 15.3 g of 2-methyl-5-nitrophenyl in 30 ml of dimethylsulfoxide is added dropwise to a mixture of 6.4 g of potassium hydroxide in 30 ml of dimethylsulfoxide. When the exothermic reaction has subsided, 19.9 g of a mixture of 2-fluoro-3-chloro-5-trifluoromethylpyridine (40% by weight) and 2,3-dichloro-5-trifluoromethylpyridine (60% by weight) are slowly added dropwise. After this exothermic reaction too has subsided, the reaction mixture is stirred for 10 hours, then poured into ice-water and extracted with dichloromethane. The organic extract is dried and concentrated by evaporation. The residue is chromatographed with a mixture of dichloromethane and hexane (in the volume ratio 35:15) over silica gel, using pure dichloromethane as eluant at the start and at the conclusion of chromatography, to give 3-(3-chloro-5-tri-fluoromethylpyridyl)-2-oxy)-4-methylnitrobenzene as a white crystalline powder with a melting point of 93°–94° C. This compound is then hydrogenated in dioxane using Raney nickel as catalyst. The catalyst is removed by filtration and the reaction solution obtained as filtrate is washed with dichloromethane and chromatographed over silica gel, affording 3-(3-chloro-5-trifluoromethylpyridyl-2-oxy)-4-methylaniline as a white crystalline powder which melts at 55° C.

FORMULATION EXAMPLES

Formulation Examples for compounds of formula I (throughout, percentages are by weight)

| 2.1 Emulsifiable concentrate | |
|---|---|
| compound 17 | 10% |
| castor oil thioxilate | 25% |
| butanol | 15% |
| ethyl acetate | 50% |

Emulsions of any required concentration can be obtained from this concentrate by dilution with water.

| 2.2 Solutions | (a) | (b) |
|---|---|---|
| compound 17 | 10% | 5% |
| ethylene glycol monomethyl ether | — | — |
| polyethylene glycol (mol. wt. 400) | 70% | — |
| N-methyl-2-pyrrolidone | 20% | — |
| epoxidised coconut oil | — | 1% |
| petroleum distillate (boiling range 160–190°) | — | 94% |

These solutions are suitable for application in the form of microdrops.

| 2.3 Granulates | (a) | (b) |
|---|---|---|
| compound 17 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 2.4 Dusts | (a) | (b) | (c) | (d) |
|---|---|---|---|---|
| compound 17 | 2% | 5% | 5% | 8% |
| highly dispersed silicic acid | 1% | 5% | — | — |
| talcum | 97% | — | 95% | — |
| kaolin | — | 90% | — | 92% |

Ready-for-use dusts are obtained by intimately mixing the carriers with the active ingredient.

| 2.5 Wettable powders | (a) | (b) | (c) | (d) |
|---|---|---|---|---|
| compound 17 | 20% | 25% | 50% | 75% |
| sodium lignosulfonate | 5% | 5% | 5% | — |
| sodium lauryl sulfate | 3% | 3% | — | 5% |
| sodium diisobutylnaphthalenesulfonate | — | — | 6% | 10 |
| octylphenol polyethylene glycol ether (7 to 8 moles of ethylene oxide) | — | — | 2% | — |
| highly dispersed silicic acid | 5% | 5% | 10% | 10% |
| kaolin | 67% | 62% | 27% | — |

The active ingredient is thoroughly mixed with the adjuvants and the mixture is thoroughly ground in a suitable mill, affording wettable powders which can be diluted with water to give suspensions of the desired concentration.

| 2.6 Extruder granulate | |
|---|---|
| compound 17 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 2.7 Coated granulate | |
|---|---|
| compound 17 | 3% |
| polyethylene glycol (mol. wt. 200) | 3% |
| kaolin | 94% |

| 2.8 Suspension concentrate | |
|---|---|
| compound 17 | 40% |
| ethylene glycol | 10% |
| nonylphenol polyethylene glycol (15 moles of ethlene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

| 2.9 Pellets or boluses | | |
|---|---|---|
| I | compound 17 | 33.0% |
| | methyl cellulose | 0.80% |
| | highly dispersed silic acid | 0.80% |
| | maize starch | 8.40% |
| II | crystalline lactose | 22.50% |
| | maize starch | 17.00% |
| | microcrystalline cellulose | 16.50% |
| | magnesium stearate | 1.00% |
| I | The methyl cellulose is stirred in water and allowed to swell. Then the silicic acid is stirred in to give a homogeneous suspension. The active ingredient and the maize starch are mixed and the aqueous suspension is added to the mix, which is kneaded to a paste. This paste is granulated through a 12M sieve and the granulate is dried. | |
| II | All 4 adjuvants are thoroughly mixed. | |
| III | Phases I and II are mixed and compressed to tablets or boluses. | |

3. BIOLOGICAL EXAMPLES

The following trails were carried out to determine the anthelmintic activity:

3.1 Trials with sheep infected with *Haemonchus contortus*

3.1.1 Activity against larval development in the host
 The test is made as a comparative test of two compounds: Closest compound of the prior art:

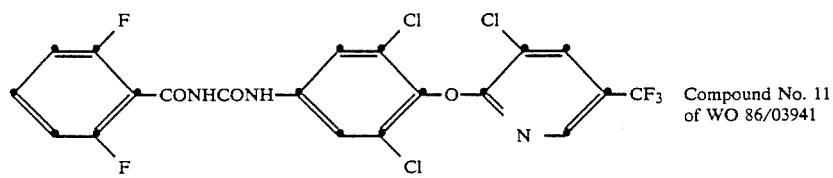

(A) Compound No. 11 of WO 86/03941 and compound according to the present invention:

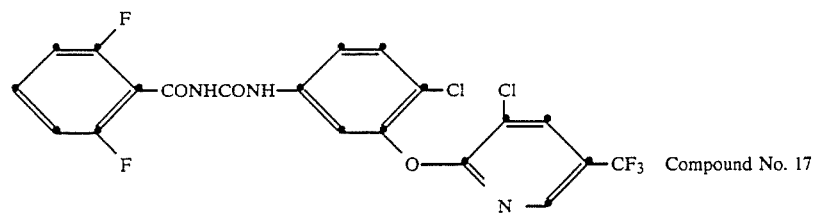

(B) Compound No. 17

The active ingredients are formulated as wettable powders according to Example 2.5 (b).

10 mg kg$^{-1}$day$^{-1}$ of the test compound is administered per os daily for 10 consecutive days. Infection with infective *H. contortus* larvae is made on the second day after the start of the treatment. Evaluation of activity is made by counting the eggs in faecal samples taken from the sheep rectally 35 days after infection.

| Compound | Dose mg kg$^{-1}$ day$^{-1}$ | Sheep No. | Faecal eggs |
|---|---|---|---|
| A | 10 | 1018 | 2300 |
|   | 10 | 980 | 4000 |
| B | 10 | 1001 | 0 |
|   | 10 | 1057 | 100 |
| Control | — | 928 | 5200 |
|   | — | 1029 | 1200 |

As is evident from the anthelmintic test above compound B, i.e. 17 of the present application exhibits a significantly better activity over the structurally closest prior art compound, namely compound A, i.e. compound No. 11 of WO-86/03941. It was unexpected from the teaching of WO 86/03941 that the movement of a 3-chloro-5-trifluoromethyl-2-pyridyloxy group in dimiloids from the para-position to the meta-position results in such a significant improvement with respect to the anthelmintic activity.

3.1.2 Activity against *H. contortus* eggs in sheep infected with adult *H. contortus*

A compound of formula I, e.g. compounds 1, 4, 5, 9, 15 to 18, 25, 26, 30, 31, 35 and 36, is administered daily at a dose of 10 mg/kg body weight with a stomach probe to sheep heavily infected with adult *H. contortus*.

Evaluation of activity is made by counting the infective larvae in incubated faecal samples taken from the sheep rectally on the 3rd and 21st day after the start of treatment. Confirmation of activity is that no larvae develop from eggs laid between the 3rd and 14th day of treatment, whereas larvae do develop from eggs laid in untreated control animals and from eggs laid after the treatment has been interrupted.

3.2 Activity against eggs of the liver fluke *Fasciola hepatica*

*F. hepatica* eggs in aqueous medium are treated with concentrations of 7.5, 75 and 750 ppm of a compound of formula I and kept in the dark for 15 days at room temperature.

Microscopic examination of the eggs after 15 days shows that no miracidia developed at the two higher concentrations and that the eggs are totally deformed.

In all three trials 3.11, 3.12 and 3.13, compounds of formula I, especially compounds 1, 4, 5, 9, 15 to 18, 25, 26, 30, 31, 35 and 36, strongly inhibit egg hatchability and larval and miracidal viability (95–100% inhibition compared with untreated hosts).

What is claimed is:

1. A method of controlling helminths in productive livestock, which comprises the step of administering to said livestock an effective amount of a compound of formula I

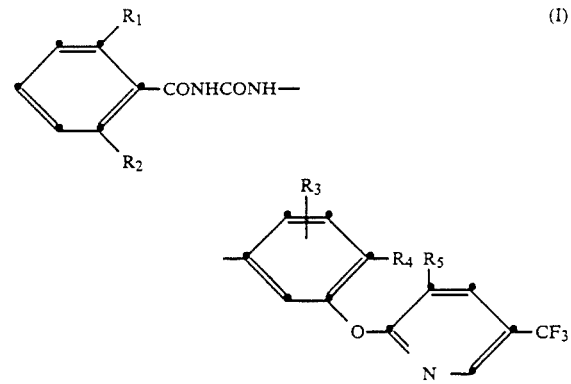

(I)

wherein
$R_1$ is $C_1$–$C_2$alkoxy, $C_1$–$C_2$alkylthio or halogen,
$R_2$ is halogen,
$R_3$ is hydrogen or halogen
$R_4$ is methyl or halogen, and
$R_5$ is chlorine.

2. A method according to claim 1, wherein
$R_1$ is fluorine, chlorine, methoxy, or methylthio,
$R_2$ is fluorine or chlorine,
$R_3$ is hydrogen, 2-fluoro or 2-chloro,
$R_4$ is fluorine, chlorine, bromine or methyl, and
$R_5$ is chlorine.

3. A method according to claim 2, wherein
$R_1$ is fluorine, methoxy or methylthio,
$R_2$ is fluorine,
$R_3$ is hydrogen,
$R_4$ is fluorine, chlorine or bromine, and $R_5$ is chlorine.

4. A method according to claim 2 wherein the compound for administration is of the formula

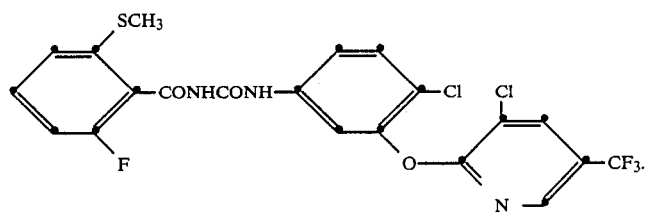

5. A method according to claim 2 wherein the compound for administration is of the formula

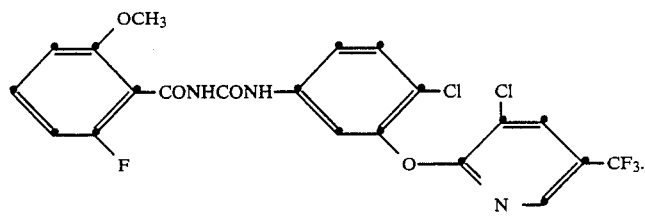

6. A method according to claim 2 wherein the compound for administration is of the formula

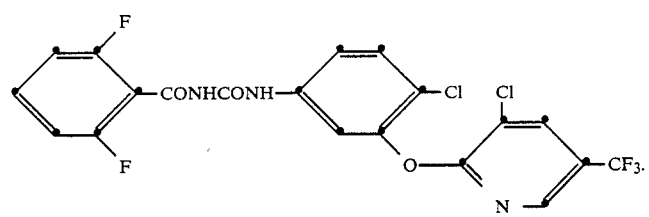

7. A method according to claim 2 wherein the compound for administration is of the formula

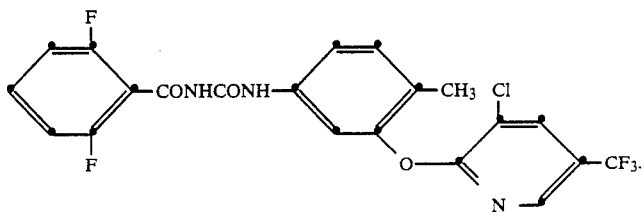

8. A method according to claim 2 wherein the compound for administration is of the formula

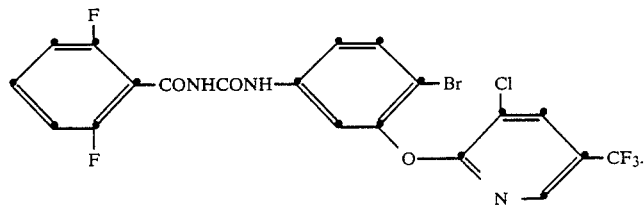

9. A method according to claim 2 wherein the compound for administration is of the formula

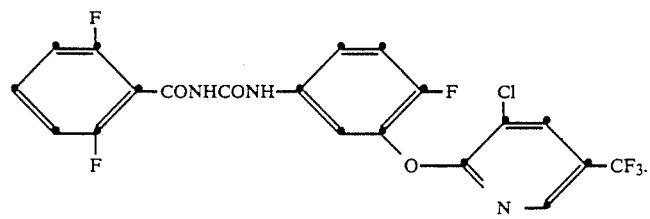
10. A method according to claim 1 wherein the active ingredient of the formula I is added to the solid or liquid feed of domestic animals so that the feed contains the active ingredient in a concentration of about 0.0005 to 0.02 percent by weight.
* * * * *